US012016865B2

(12) United States Patent
DiLuccio et al.

(10) Patent No.: US 12,016,865 B2
(45) Date of Patent: Jun. 25, 2024

(54) METHODS AND PHARMACEUTICAL COMPOSITIONS FOR TREATING CANDIDA AURIS IN BLOOD

(71) Applicant: Cormedix Inc., Berkeley Heights, NJ (US)

(72) Inventors: Robert DiLuccio, Haymarket, VA (US); Bruce Reidenberg, Rye, NY (US)

(73) Assignee: Cormedix Inc., Berkeley Heights, NJ (US)

( * ) Notice: Subject to any disclaimer, the term of this patent is extended or adjusted under 35 U.S.C. 154(b) by 0 days.

(21) Appl. No.: 16/229,898

(22) Filed: Dec. 21, 2018

(65) Prior Publication Data

US 2019/0192529 A1 Jun. 27, 2019

Related U.S. Application Data

(60) Provisional application No. 62/608,843, filed on Dec. 21, 2017.

(51) Int. Cl.
| | | |
|---|---|---|
| *A61K 31/549* | (2006.01) | |
| *A61K 9/48* | (2006.01) | |
| *A61K 9/51* | (2006.01) | |
| *A61K 47/54* | (2017.01) | |
| *A61P 31/10* | (2006.01) | |

(52) U.S. Cl.
CPC .......... *A61K 31/549* (2013.01); *A61K 9/4833* (2013.01); *A61K 9/4891* (2013.01); *A61K 9/5161* (2013.01); *A61K 47/555* (2017.08); *A61P 31/10* (2018.01)

(58) Field of Classification Search
CPC .................................................. A61K 31/549
See application file for complete search history.

(56) References Cited

U.S. PATENT DOCUMENTS

| | | | |
|---|---|---|---|
| 3,423,408 | A | 1/1969 | Pfirrmann |
| 4,107,305 | A | 8/1978 | Pfirrmann |
| 4,337,251 | A | 6/1982 | Pfirrmann |
| 4,587,268 | A | 5/1986 | Pfirrmann |
| 4,604,391 | A | 8/1986 | Pfirrmann |
| 4,605,691 | A | 8/1986 | Balazs et al. |
| 4,626,536 | A | 12/1986 | Pfirrmann |
| 4,772,468 | A | 9/1988 | Pfirrmann |
| 4,882,149 | A | 11/1989 | Spector |
| 9,175,027 | B2 | 11/2015 | Wu |
| 2012/0202890 | A1 | 8/2012 | Wu |
| 2012/0202979 | A1 | 8/2012 | Wu |
| 2016/0229979 | A1 | 8/2016 | Katayama |
| 2017/0056561 | A1 | 3/2017 | DiLuccio et al. |
| 2017/0100407 | A1 | 4/2017 | Reidenberg et al. |
| 2017/0196875 | A1 | 7/2017 | DiLuccio |

FOREIGN PATENT DOCUMENTS

| | | |
|---|---|---|
| CH | 482713 | 12/1969 |
| GB | 1124285 | 8/1968 |
| WO | WO 2005/115357 | 12/2005 |
| WO | WO 2012/109112 | 8/2012 |
| WO | WO 2013/003306 | 1/2013 |

OTHER PUBLICATIONS

Reidenberg et al. ASM MIcrobe Conference, Jun. 2017, Abstract.*
Lee et al. Adv. Drug. Deliv. Rev., 2016, Vlol. 107, pp. 176-191.*
Khunmanee et al. (Journal of Tissue Engineering, Sep. 2017, vol. 8, pp. 1-16.*
Farrington, M. Clinical Pharmacology, 2012, 11th Edition, p. 1.*
Salouti et al. Application of Nanotechnology in Drug delivery; Title: Nanoparticle based Drug Delivery Systems for Treatment of Infectious Diseases, 2014; pp. 1-22.*
Adams, Monica L. et al., Amphiphilic Block Copolymers for Drug Delivery, Journal of Pharmaceutical Sciences, vol. 92, No. 7, 2003, pp. 1343-1355.
Cherian, Anitha K et al., Self-Assembled Carbohydrate-Stabilized Ceramic Nanoparticles for the Parenteral Delivery of Insulin, Drug Development and Industrial Pharmacy, vol. 26, No. 4, 2000, pp. 459-463.
Cremophor-based paclitaxel 'chemo' drug triggers fatal allergic reactions, The Medical News, 2009.
Duncan, Ruth, The dawning era of polymer therapeutics, Nature Revies Drug Discovery, vol. 2, 2003, pp. 347-360.
Gursoy, R. Neslihan et al., Self-emulsifying drug delivery systems (SEDDS) for improved oral delivery of lipophilic drugs, Biomedicine & Pharmacotherapy, vol. 58, 2004, 173-18.
Kaur, Indu Pal et al., Potential of solid lipid nanoparticles in brain targeting, Journal of Controlled Release, vol. 127, 2008, pp. 97-109.
Kohane, Daniel et al., Biocompatibility of lipid-protein-sugar particles containing bupivacaine in the epineurium, Journal of Biomedical Materials Research, vol. 59, No. 3, 2002, pp. 450-459.
Kohane, Daniel et al., Sciatic Nerve Blockade with Lipid-Protein-Sugar Particles Containing Bupivacaine, Pharmaceutical Research, vol. 17, No. 10, 2000, pp. 1243-1249.
Kumar et al., Itraconazole—resistant Candida auris with phospholipase, proteinase and hemolysin activity from a case of vulvovaginitis, The Journal of Infection in Developing Countries, 2015; 9(4):435-437.
Lian, Tianshun et al., Trend and developments in Liposome Drug Delivery Systems, Journal of Pharmaceutical Sciences, vol. 90, No. 6, 2001, pp. 667-680.
Lipinski, Christopher A., Drug-like properties and the causes of poor solubility and poor permeability, J Pharmacol Toxicol Method, vol. 44, 2000, pp. 235-249.
Myers et al., The Relationship between Structure and Activity of Taurolin, Journal of Applied Microbiology, vol. 48, Issue 1, Feb. 1980, pp. 89-96.

(Continued)

*Primary Examiner* — Svetlana M Ivanova
(74) *Attorney, Agent, or Firm* — Pandiscio & Pandiscio

(57) ABSTRACT

A method for treating *Candida auris* in blood, comprising administering to the blood taurolidine, and/or one or more taurolidine derivatives, in a concentration which is effective to treat *C. auris* in the blood.

14 Claims, 2 Drawing Sheets

(56) References Cited

OTHER PUBLICATIONS

Na, Man et al., Dendrimers as potential drug carriers. Part II. Prolonged delivery of ketoprofen by in vitro and in vivo studies, European Journal of Medicinal Chemistry, vol. 41, 2006, pp. 670-674.

Thayer, Ann M., Finding Solutions: Custom manufacturers take on drug solubility issues to help pharmaceutical firms move products through development, Chemical & Engineering News, vol. 88, No. 22, 2010, pp. 13-18.

Tsay et al., Centers for Disease Control and Prevention, Notes from the Field: Ongoing Transmission of Candida auris in Health Care Facilities—United States, Jun. 2016-May 2017, May 19, 2017, https://www.cdc.gov/mmwr/volumes/66/wr/mm6619a7.htm.

Wang, Taoran et al., Preparation of ultra-fine powders from polysaccharide-coated solid lipid nanoparticles and nanostructured lipid carriers by innovative nano spray drying technology, Int J Pharm., vol. 511, 2016, pp. 219-222.

Bandara, H. M. N. H., et al., Future therapies targeted towards elimnating Candida biofilms and associated infections, Expert Review of Anti-Infective Therapy, vol. 15, No. 3, 2017, pp. 299-318.

Cormedix Inc., Cormedix Inc. Provides Comprehensive Pipeline Update During Research and Development Day, 2017.

Reidenberg, B. et al., Multi-Resistant Candida auris is Susceptible to Taurolidine, Aspergillus and Aspergillosis, Oct. 25, 2017, https://www.aspergillus.org.uk/conference_abstracts/multi-resistant-candida-auris-is-susceptible-to-taurolidine/.

Dreborg, S. et al., Immunotherapy with Monomethoxypolyethylene Glycol Modified Allergens, Crit Rev Ther Drug Carrier Syst., 1990, vol. 6, No. 4, Abstract.

Duncan, R. et al., Soluble Synthetic Polymers as Potential Drug Carriers, Advances in Polymer Science, 1984, vol. 57, pp. 53-101.

Menei, P. et al., Biodegradation and Brain Tissue Reaction to Poly (D,L-lactide-co-glycolide) Microspheres, Biomaterials., 1993, vol. 14, No. 6, pp. 470-478.

Monsigny, M. et al., Glycoconjugates as Carriers for Specific Delivery of Therapeutic Drugs and Genes, J. Advanced Drug Delivery Reviews, 1994, vol. 14, pp. 1-24.

Palomino E., 'Carbohydrate Handles' as Natural Resources in Drug Delivery, Advanced Drug Delivery Reviews, 1994, vol. 13, pp. 311-323.

Pang, et al., Final Report on the Safety Assessment of Polyethylene Glycols (PEGs) -6, -8, -32, -75, -150, -14M, -20M, Journal of the American College of Toxicology, 1993, vol. 12, No. 5, pp. 429-457.

Yamaoka, T. et al., Distribution and Tissue Uptake of Poly(ethylene glycol) with Different Molecular Weights after Intravenous Administration to Mice, Journal of Pharmaceutical Sciences, 1994, vol. 83, No. 4, pp. 601-606.

Mouton, J. et al., MIC-based dose adjustment: facts and fables, Journal of Antimicrobial Chemotherapy, Dec. 5, 2017, vol. 73, pp. 564-568.

Veronese F. et al., The Impact of PEGylation on Biological Therapies, Biodrugs, 2008, No. 5, vol. 22, pp. 315-329.

* cited by examiner

TAUROLIDINE MECHANISM OF ACTION

| Collection No | Organism | Year | Site Code | Read Date | Taurolidine MIC 24hr_50% | Taurolidine MIC 48hr_50% | Taurolidine MIC 24hr_100% | Taurolidine MIC 48hr_100% | AmphotericinB MIC 24hr_50% | AmphotericinB MIC 48hr_50% | AmphotericinB MIC 24hr_100% | AmphotericinB MIC 48hr_100% | Fluconazole MIC 24hr_50% | Fluconazole MIC 48hr_50% | Fluconazole MIC 24hr_100% | Fluconazole MIC 48hr_100% |
|---|---|---|---|---|---|---|---|---|---|---|---|---|---|---|---|---|
| 800104 | Candida auris | 2013 | JMI | 4/27/2017 | 256 | 512 | 512 | 512 | 0.5 | 1 | 1 | 1 | 128 | >128 | >128 | >128 |
| 800106 | Candida auris | 2013 | JMI | 4/27/2017 | 256 | 512 | 512 | 512 | 0.5 | 1 | 1 | 1 | >128 | >128 | >128 | >128 |
| 800108 | Candida auris | 2013 | JMI | 4/27/2017 | 256 | 512 | 512 | 512 | 1 | 1 | 1 | 1 | 32 | >128 | >128 | >128 |
| 800115 | Candida auris | 2013 | JMI | 4/27/2017 | 256 | 512 | 512 | 512 | 1 | 1 | 1 | 1 | 128 | >128 | >128 | >128 |
| 800119 | Candida auris | 2013 | JMI | 4/27/2017 | 256 | 512 | 512 | 512 | 1 | 1 | 1 | 2 | 128 | >128 | >128 | >128 |
| 800122 | Candida auris | 2013 | JMI | 4/27/2017 | 512 | 512 | 512 | 512 | 1 | 1 | 1 | 1 | >128 | >128 | >128 | >128 |
| 871779 | Candida auris | 2014 | 350 | 4/27/2017 | 512 | 512 | 512 | 512 | 1 | 1 | 1 | 1 | 64 | 128 | 128 | >128 |
| 899807 | Candida auris | 2015 | 129 | 4/27/2017 | 512 | 512 | 512 | 512 | 1 | 2 | 2 | 2 | >128 | >128 | >128 | >128 |
| 968647 | Candida auris | 2016 | 136 | 4/27/2017 | 512 | 512 | 512 | 512 | 1 | 2 | 2 | 2 | >128 | >128 | >128 | >128 |
| 968648 | Candida auris | 2016 | 136 | 4/27/2017 | 256 | 512 | 512 | 512 | 1 | 2 | 2 | 2 | >128 | >128 | >128 | >128 |
| 999469 | Candida auris | 2017 | JMI | 4/27/2017 | 256 | 512 | 512 | 512 | 0.5 | 1 | 1 | 1 | 2 | 2 | 2 | 8 |
| 999470 | Candida auris | 2017 | JMI | 4/27/2017 | 256 | 512 | 512 | 512 | 1 | 1 | 1 | 4 | 4 | 16 | >128 | >128 |
| 999471 | Candida auris | 2017 | JMI | 4/27/2017 | 256 | 512 | 512 | 512 | 1 | 1 | 1 | 1 | >128 | >128 | >128 | >128 |
| 999472 | Candida auris | 2017 | JMI | 4/27/2017 | 256 | 512 | 512 | 512 | 1 | 1 | 1 | 1 | >128 | >128 | >128 | >128 |
| 999473 | Candida auris | 2017 | JMI | 4/27/2017 | 512 | 512 | 512 | 1024 | 1 | 1 | 1 | 1 | >128 | >128 | >128 | >128 |
| 999474 | Candida auris | 2017 | JMI | 4/27/2017 | 512 | 512 | 512 | 1024 | 0.5 | 1 | 1 | 1 | >128 | >128 | >128 | >128 |
| 999475 | Candida auris | 2017 | JMI | 4/27/2017 | 512 | 512 | 512 | 512 | 2 | 2 | 2 | 2 | >128 | >128 | >128 | >128 |
| 999476 | Candida auris | 2017 | JMI | 4/27/2017 | 512 | 512 | 512 | 1024 | 2 | 2 | 2 | 2 | >128 | >128 | >128 | >128 |
| 999477 | Candida auris | 2017 | JMI | 4/27/2017 | 512 | 512 | 512 | 1024 | 2 | 2 | 2 | 2 | >128 | >128 | >128 | >128 |
| 999478 | Candida auris | 2017 | JMI | 4/27/2017 | 512 | 512 | 512 | 512 | 1 | 2 | 2 | 2 | >128 | >128 | >128 | >128 |
| | | | | | MIC50/MIC90 | | | | MIC50/MIC90 | | | | MIC50/MIC90 | | | |
| | | | | | 512/512 | 512/512 | 512/512 | 512/1024 | 1/1 | 1/2 | 1/2 | 1/2 | >128/>128 | >128/>128 | >128/>128 | >128/>128 |

MIC results in mg/L

MIC = minimum inhibitory concentration, which is the lowest concentration of the drug which presents visible growth of bacterium - thus, cell entries identify the lowest concentration (in mg/L) of the drug which achieves the identified kill ratio (e.g., 50%, 100%) in the identified time (e.g., 24 hr, 48 hr)

FIG. 2

METHODS AND PHARMACEUTICAL COMPOSITIONS FOR TREATING CANDIDA AURIS IN BLOOD

REFERENCE TO PENDING PRIOR PATENT APPLICATION

This patent application claims benefit of pending prior U.S. Provisional Patent Application Ser. No. 62/608,843, filed Dec. 21, 2017 by CorMedix, Inc. and Robert DiLuccio et al. for METHODS AND PHARMACEUTICAL COMPOSITIONS FOR TREATING Candida auris IN BLOOD, which patent application is hereby incorporated herein by reference.

FIELD OF THE INVENTION

This invention relates generally to methods and pharmaceutical compositions for treating a patient, and more particularly to methods and pharmaceutical compositions for treating candida auris in blood.

BACKGROUND OF THE INVENTION

1. *Candida auris* in General

*Candida auris* is a species of fungus which grows as yeast, first described in 2009. It is one of the few species of the *Candida* genus which causes candidiasis (a fungal infection caused by *candida*) in humans. Candidiasis is often acquired in hospitals by patients with weakened immune systems. *Candida auris* (sometimes also referred to as *C. auris*) can cause invasive candidiasis in which the bloodstream (fungemia), the central nervous system, internal organs, etc. are infected. *Candida auris* has recently attracted increased attention because of its multidrug resistance. Treatment is also complicated because it is easily misidentified as other *Candida* species.

2. Clinical Significance

As noted above, *Candida auris* (*C. auris*) is one of the few *Candida* species which can cause candidiasis in humans, and is often acquired in hospitals by patients with weakened immune systems. It can cause invasive candidiasis, in which the blood stream (fungemia), the central nervous system, internal organs (e.g., kidneys, liver, spleen, etc.), bones, muscles, joints, eyes, etc. are invaded. *C. auris* has attracted increased clinical attention because of its multidrug resistance.

As also noted above, treatment is complicated because *C. auris* is easily misidentified as other *Candida* species.

A brief outline of the clinical relevance of *C. auris*, as of 2016, understandable by general audiences, was published by the Center for Infectious Disease Research and Policy at the University of Minnesota.

3. History

*C. auris* was first described after it was isolated from the ear canal of a 70-year-old Japanese woman at the Tokyo Metropolitan Geriatric Hospital in Japan. It was isolated based on its ability to grow in the presence of the fungicide micafungin, an echinocandin class fungicide. Phenotypic, chemotaxonomic and phylogenetic analyses of the strain established *C. auris* as a new strain of the genus *Candida*.

The first three cases of disease-causing *C. auris* were reported from South Korea in 2011. Two isolates had been obtained during a 2009 study, and a third was discovered in a stored sample from 1996. All three cases had persistent fungemia, i.e., bloodstream infection, and two of the patients subsequently died due to complications from the bloodstream infection. Notably, the isolates were initially misidentified as *Candida haemuloni* and *Rhodotorula glutinis* using standard methods, until DNA sequence analysis correctly identified them as *C. auris*. These first cases emphasize the importance of accurate species identification and timely application of the correct antifungal for the effective treatment of candidiasis with *C. auris*.

During 2009-2011, twelve *C. auris* isolates were obtained from patients at two hospitals in Delhi, India. The same genotype was found in distinct settings: intensive care, surgical, medical, oncologic, neonatal, and pediatric wards, which were mutually exclusive with respect to healthcare personnel. Most of these patients had persistent candidemia and a high mortality rate was observed. All isolates were of the same clonal strain and were only identified positively by DNA sequence analysis (as previously, the strain was misidentified using established diagnostic laboratory tests). The Indian researchers wrote in 2013 that *C. auris* was believed to be much more prevalent than reported, since most diagnostic laboratories do not use DNA sequence-based methods for strain identification and hence the prevalence of *C. auris* was almost certainly underrecognized.

The *C. auris* fungus spread to other continents, and in early 2016, a multi-drug-resistant strain was eventually discovered in Southeast Asian countries. The first report of *C. auris* in Europe was an October 2016 outbreak in Royal Brompton Hospital, a London cardio-thoracic hospital.

In April 2017, CDC director Anne Schuchat named *C. auris* as a "catastrophic threat". As of May 2017, the CDC had reported 77 cases of *C. auris* in the United States on its website. Of these, 69 cases were from samples collected in New York and New Jersey.

Thus there is a need for an effective approach for treating *C. auris* infections, and particularly blood-borne infections of *C. auris*.

SUMMARY OF THE INVENTION

The present invention relates to methods and pharmaceutical compositions for treating a blood-borne infection of *C. auris*.

More particularly, the present invention relates to the use of 4,4'-methylene-bis(tetrahydro-1,2,4-thiadiazine)-1,1,1', 1',-tetraoxide, commonly known as taurolidine, and/or taurolidine derivatives (see below) for neutralizing *C. auris* blood-borne pathogens.

In accordance with the present invention, taurolidine, and/or taurolidine derivatives (see below), can be incorporated into a pharmaceutical composition, and formulated with an appropriate carrier acceptable for parenteral delivery of the compound, so as to treat *C. auris* in blood.

A key aspect of the present invention is providing the taurolidine, and/or the taurolidine derivatives (see below), with a prolonged period of hydrolysis in the vicinity of the *C. auris* pathogen so that the active moieties of the taurolidine, and/or the taurolidine derivatives (see below), released by the hydrolysis process, can be highly effective against the *C. auris* pathogen. To this end, the taurolidine, and/or the taurolidine derivatives (see below) is provided in, preferably:

(i) a degradable nanoparticle incorporating the taurolidine, and/or the taurolidine derivatives (see below), e.g., a solid taurolidine core covered by a solid excipient coating, or a liquid taurolidine core covered by a solid excipient coating, or a liquid taurolidine core carried by a porous body which is then sealed with a solid excipient coating, etc. (note: for the purposes of the present invention, the term nanoparticle is intended to include any particle having nanoscale-sized dimensions or larger, including micro-sized dimensions);

(ii) a polymer-based system wherein the taurolidine, and/or the taurolidine derivatives (see below), is/are bound to the polymer for delivery to the therapy site, e.g., a PEGylated system wherein the taurolidine, and/or the taurolidine derivatives, is/are bound to polyethylene glycol (PEG) for delivery to the therapy site;

(iii) a suspension of solid taurolidine-containing, and/or taurolidine derivative-containing (see below), particles;

(iv) a pro-drug providing taurolidine, and/or taurolidine derivatives (see below); or (v) a taurolidine-containing, and/or taurolidine derivative-containing (see below), solution capable of prolonging the effect of the taurolidine, and/or the taurolidine derivatives (see below).

In one preferred form of the invention, there is provided a method for treating *Candida auris* in blood, comprising administering to the blood taurolidine, and/or one or more taurolidine derivatives, in a concentration which is effective to treat *C. auris* in the blood.

In another preferred form of the invention, there is provided a pharmaceutical composition comprising:
  a nanoparticle comprising:
    a core comprising taurolidine, and/or one or more taurolidine derivatives; and
    a hydrolysable covering temporarily shielding the core.

In another preferred form of the invention, there is provided a pharmaceutical composition comprising taurolidine, and/or the one or more taurolidine derivatives, bound to a polymer.

In another preferred form of the invention, there is provided a pharmaceutical composition comprising taurolidine, and/or one or more taurolidine derivatives, dispersed in a polymer-carbohydrate-lipid conjugate or polymer-carbohydrate-lipid conjugates.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 2 is a table showing the effectiveness of treating a blood-borne infection of *C. auris* using taurolidine and/or taurolidine derivatives.

DETAILED DESCRIPTION OF THE PREFERRED EMBODIMENTS

1. Taurolidine in General

Figure 1:
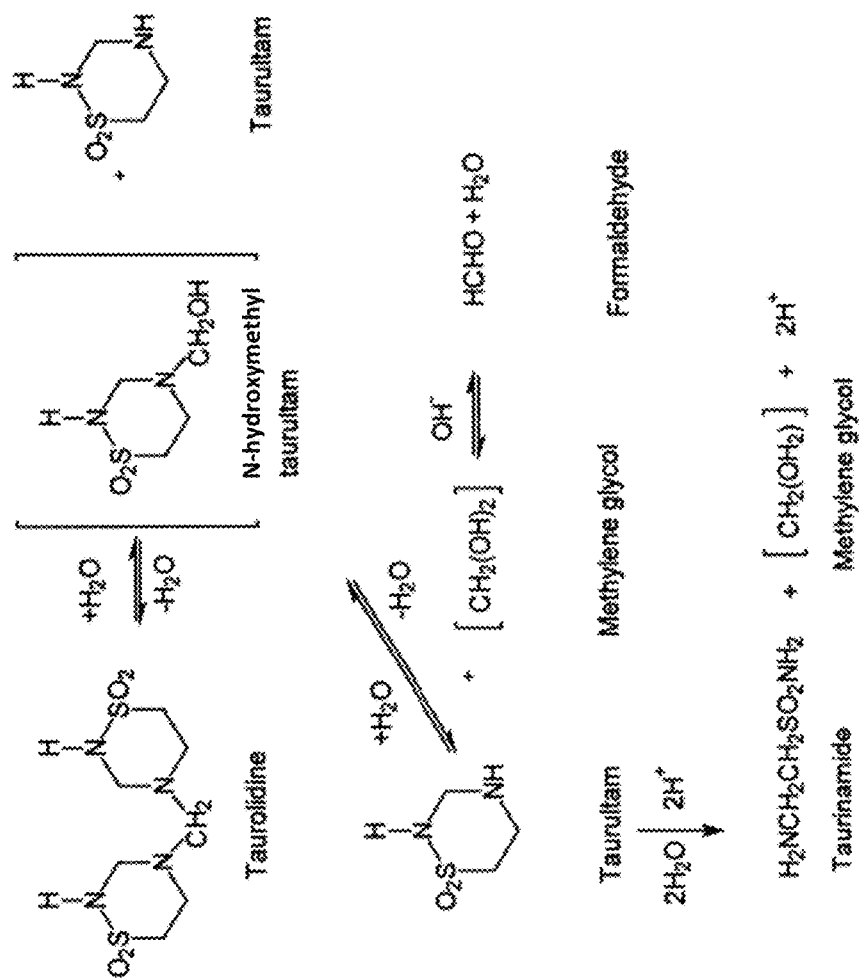
FIG. 1 is a schematic view showing the mechanism of action for taurolidine.

Taurolidine (4,4'-methylene-bis(tetrahydro-1,2,4-thiadiazine)-1,1,1',1',-tetraoxide), and/or taurolidine derivatives (see below), are known to have antimicrobial and antilipopolysaccharide properties. Taurolidine, and/or taurolidine derivatives (see below), are also known to provide antiflammatory properties. The immunomodulatory action of taurolidine, and/or taurolidine derivatives (see below), is reported to be mediated by priming and activation of macrophages and polymorphonuclear leukocytes.

Taurolidine is derived from the amino acid taurine. In aqueous solution, the parent molecule taurolidine forms an equilibrium with N-hydroxymethyl taurultam and taurultam, with taurinamide, methylene glycol and formaldehyde being downstream derivatives. For the purposes of the present invention, N-hydroxymethyl taurultam, taurultam, taurinamide, methylene glycol and formaldehyde can all be considered taurolidine derivatives. See FIG. 1, which shows taurolidine's mechanism of action.

The active moieties of taurolidine, and/or the taurolidine derivatives, are believed to be the derivative methylol groups which react with the bacterial cell wall, the cell membrane, and the proteins of the cell membrane, as well as with the primary amino groups of endo- and exotoxins. Microbes are killed and the resulting toxins are inactivated; the destruction time in vitro is approximately 30 minutes.

Taurolidine occurs as a white to off-white powder having the molecular formula $C_7H_{16}N_4O_4S_2$ and a melting point of 154 degrees C.

Taurolidine's general characteristics include acceptable stability in the solid state when stored at ambient conditions, melting with decomposition at approximately 170 degrees C., and the following solubility in aqueous solutions and organic solvents:
  Water: 1% at 20 degrees C.
  Dilute HCl: soluble
  Dilute NaOH: soluble
  $CHCl_3$: insoluble
  EtOH: sparingly soluble
  DMF: 1 g in 2 mL at approx. 60 degrees C.
  Acetone: 1 g in 120 mL
  Boiling Ethanol: 1 g in 130 mL
  Boiling Methanol: 1 g in 170 mL
  Boiling Ethyl Acetate: 1 g in 200 mL A saturated solution of taurolidine in deionized water has a pH of 7.4, approximately the pH of blood. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents (including U.S. Pat. No. 3,423,408; Switzerland Patent No. 482,713; and United Kingdom Patent No. 1,124,285) and is carried out in five stages:

(1) potassium phthalimidoethane sulphonate is prepared from taurine, phthalic anhydride, glacial acetic acid and potassium acetate;

(2) potassium phthalimidoethane sulphonate is then converted to phthalimidoethane sulphonylchloride by chlorination with phosphorous oxychloride;

(3) phthalimidoethane sulphonylchloride is reacted with ammonia to form phthalimidoethane sulphonamide;

(4) phthalimidoethane sulphonamide is reacted with hydrazine hydrate to form taurinamide hydrochloride; and (5) taurolidine is prepared from the taurinamide hydrochloride and formaldehyde.

The antimicrobial actions of taurolidine have been described in U.S. patent application Ser. No. 09/151,885, filed Sep. 11, 1998; in U.S. Pat. No. 3,423,408; and elsewhere in the literature. In addition, the following United States patents describe various uses for, and compositions containing, taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine has been shown to be safe and well tolerated at systemic doses exceeding 40 g/day and cumulative doses up to, and exceeding, 300 g.

2. The Novel Pharmaceutical Composition of the Present Invention

It has now been discovered that taurolidine, and/or taurolidine derivatives, can be applied to a blood-borne infection of *C. auris* so as to neutralize *C. auris* blood-borne pathogens. See, for example, FIG. 2, which shows the effectiveness of treating *C. auris* blood-borne pathogens with taurolidine and/or taurolidine derivatives.

In accordance with the present invention, taurolidine, and/or taurolidine derivatives, can be incorporated into a pharmaceutical composition, and formulated with an appropriate carrier acceptable for parenteral delivery of the compound, so as to treat *C. auris* in blood.

A key aspect of the present invention is providing the taurolidine, and/or the taurolidine derivatives, with a prolonged period of hydrolysis in the vicinity of the *C. auris* pathogen so that the active moieties of the taurolidine, and/or the taurolidine derivatives, released by the hydrolysis process, can be highly effective against the *C. auris* pathogen. To this end, the taurolidine, and/or the taurolidine derivatives, is/are provided in, preferably:
   (i) a degradable nanoparticle incorporating the taurolidine, and/or the taurolidine derivatives, e.g., a solid taurolidine core covered by a solid excipient coating, or a liquid taurolidine core covered by a solid excipient coating, or a liquid taurolidine core carried by a porous body which is then sealed with a solid excipient coating, etc. (note: for the purposes of the present invention, the term nanoparticle is intended to include any particle having nanoscale-sized dimensions or larger, including micro-sized dimensions);
   (ii) a polymer-based system wherein the taurolidine, and/or the taurolidine derivatives, is/are bound to the polymer for delivery to the therapy site, e.g., a PEGylated system wherein the taurolidine, and/or the taurolidine derivatives, is/are bound to polyethylene glycol (PEG) for delivery to the therapy site;
   (iii) a suspension of solid taurolidine-containing, and/or taurolidine derivative-containing, particles;
   (iv) a pro-drug providing taurolidine and/or taurolidine derivatives; or
   (v) a taurolidine-containing, and/or taurolidine derivative-containing, solution capable of prolonging the effect of the taurolidine, and/or the taurolidine derivatives.

The taurolidine should itself be buffered (and, if desired, the taurolidine derivatives may also be buffered) to the pH of blood, i.e., to between 7.5 and 7.4, and the pharmaceutical composition can advantageously contain substances that increase the cellular permeability for the novel taurolidine-containing pharmaceutical composition.

The novel taurolidine-containing, and/or taurolidine derivative-containing, pharmaceutical compositions suitable for introduction into the blood may be in the form of powders, solutions (e.g., aqueous solutions) or suspensions, buffered to pH 7.5-7.4, and can be formulated with anticoagulants and preservatives usually incorporated in parenteral dosage forms.

According to the present invention, there is provided novel pharmaceutical compositions comprising taurolidine, and/or taurolidine derivatives, with one or more carriers (which are excipients). The carriers may, for example, be those conventional for such forms and may include gelatin, sterile water, and/or suspending, emulsifying, dispersing, thickening or gelling agents.

The pharmaceutical compositions of the present invention, in the form of powders, solutions or suspensions, may contain taurolidine at a concentration of preferably between about 0.10% and about 20.0% by weight, and more preferably between about 0.5% and about 2.0% by weight for solutions (e.g., aqueous solutions) or suspensions, or up to about 10% by weight for powders. The formulations of taurolidine in the present invention are preferably about 0.5%, 1.0%, 2.0% or 4.0% w/volume.

The amounts of taurolidine, and/or taurolidine derivatives, introduced into the blood may vary according to the concentration of the *C. auris* pathogens in the blood and are adjusted such that the amount of taurolidine, and/or taurolidine derivatives, is sufficient to treat the *C. auris* present in the blood.

3. Nanoparticles 3.1 Nanoparticle Delivery System

In one form of the invention, the hydrolysable taurolidine, and/or the taurolidine derivatives, is encapsulated within a hydrolysable coating (which is an excipient) so as to form nanoparticles (comprising taurolidine, and/or taurolidine derivative, centers and hydrolysable excipient coatings) so that the hydrolysable coating covers the hydrolysable taurolidine, and/or the taurolidine derivatives, as the mixture is introduced into the blood, protecting the hydrolysable taurolidine, and/or taurolidine derivatives, from hydrolyzing too quickly in the blood. Thereafter, the hydrolysable coating is hydrolyzed, exposing the hydrolysable taurolidine, and/or taurolidine derivatives, to the blood, whereupon the hydrolysable taurolidine, and/or taurolidine derivatives, is/are hydrolyzed to its active moieties (i.e., methylol groups), whereby to provide local antimicrobial effect to treat the *C. auris* pathogen. In this way, encapsulation of the hydrolysable taurolidine, and/or the taurolidine derivatives, delays hydrolysis of the taurolidine, and/or taurolidine derivatives, so as to provide long lasting antimicrobial action against the *C. auris* pathogen.

In other words, in one form of the invention, the hydrolysable taurolidine, and/or the taurolidine derivatives, is/are covered by a hydrolysable coating (which is an excipient), with the hydrolysable taurolidine, and/or the taurolidine derivatives, being encapsulated by the hydrolysable coating, i.e., so as to form nanoparticles. When the nanoparticles are introduced into the blood, the hydrolysable excipient coating initially protects the hydrolysable taurolidine, and/or the taurolidine derivatives, from premature hydrolysis. As the hydrolysable coating is hydrolyzed, the hydrolysable taurolidine, and/or the taurolidine derivatives, is/are exposed to the blood, whereupon the taurolidine, and/or the taurolidine derivatives, hydrolyze(s) into its active moieties (i.e., methylol groups) which treat the *C. auris* infection (or prevent recurrence of the *C. auris* infection). In this way, encapsulation of the hydrolysable taurolidine, and/or the taurolidine derivatives, delays hydrolysis of the taurolidine, and/or the taurolidine derivatives, so as to provide long lasting antimicrobial action against the *C. auris* pathogen.

Note: for the purposes of the present invention, the term nanoparticle is intended to include any particle having nanoscale-sized dimensions or larger, including micro-sized dimensions.

In one preferred form of the invention, the nanoparticle comprises a solid taurolidine core covered by a solid excipient coating.

In another preferred form of the invention, the nanoparticle comprises a liquid taurolidine core covered by a solid excipient coating.

In still another preferred form of the invention, the nanoparticle comprises a liquid taurolidine core carried by a porous body which is then sealed with a solid excipient coating.

In one form of the invention, the hydrolysable excipient coating comprises, for example, a solid, slowly absorbing polymer. By way of example but not limitation, the polymer coating may comprise polylactide or polylactate.

In one form of the invention, the solid excipient coating may comprise a polysaccharide that specifically binds to fungal mannoproteins, most preferably non-digestible polysaccharides. By way of example but not limitation, in one preferred form of the invention, the polysaccharide coating may comprise chitosan, starch or alginate.

In one preferred form of the invention, the nanoparticles are delivered to the blood in a suitable pharmaceutical carrier, e.g., a fluid. In one preferred form of the invention, the suitable pharmaceutical carrier may comprise a hyaluronic acid hydrogel.

3.2 the Taurolidine Nanoparticle

The taurolidine nanoparticle comprises a taurolidine, and/or taurolidine derivative, center encapsulated by an excipient coating.

In one preferred form of the invention, the nanoparticle comprises a solid taurolidine core covered by a solid excipient coating. By way of example but not limitation, the solid taurolidine core may be formed out of taurolidine powder, and the solid excipient coating may be formed out of a solid, slowly absorbing polymer, e.g., one comprising polylactide or polylactate. In one preferred form of the invention, the solid excipient coating may comprise a polysaccharide that specifically binds to fungal mannoproteins, most preferably non-digestible polysaccharides. By way of example but not limitation, in one preferred form of the invention, the polysaccharide coating may comprise chitosan, starch or alginate.

In another preferred form of the invention, the nanoparticle comprises a liquid taurolidine core covered by a solid excipient coating. By way of example but not limitation, the liquid taurolidine core may be formed out of a taurolidine solution or suspension in oil, preferably nutritive, most preferably medium chain triglyceride, at a concentration of from 1,000 mcg/mL to 5,000 mcg/mL, and most preferably 3,000 mcg/mL, and the solid excipient coating may be formed out of a solid, slowly absorbing polymer, e.g., one comprising polylactide or polylactate. In one preferred form of the invention, the solid excipient coating may comprise a polysaccharide that specifically binds to fungal mannoproteins, most preferably non-digestible polysaccharides. By way of example but not limitation, in one preferred form of the invention, the polysaccharide coating may comprise chitosan, starch or alginate.

In another preferred form of the invention, the nanoparticle comprises a liquid taurolidine core carried by a porous body which is then sealed with a solid excipient coating. By way of example but not limitation, the taurolidine core comprises a taurolidine solution or suspension in oil, preferably nutritive, most preferably medium chain triglyceride, at a concentration of from 1,000 mcg/mL to 5,000 mcg/mL, and most preferably 3,000 mcg/mL. The liquid taurolidine core is contained within a porous body and then sealed with a solid excipient coating so as to form the taurolidine nanoparticle. By way of example but not limitation, the taurolidine core may be contained within a porous silicate sphere or a carbon nanotube. Where the taurolidine is contained within a porous silicate sphere or a carbon nanotube, the openings ("pores") of the porous silicate sphere or nanotube may be closed off with a coating of a solid, slowly absorbing polymer, e.g., one comprising polylactide or polylactate. In one preferred form of the invention, where the taurolidine is contained within a porous silicate sphere or carbon nanotube, the openings ("pores") of the sphere or nanotube may be closed off with a coating of polysaccharide that specifically binds to fungal mannoproteins, most preferably non-digestible polysaccharides. By way of example but not limitation, in one preferred form of the invention, the polysaccharide coating may comprise chitosan, starch or alginate.

3.3 Manufacturing the Taurolidine Nanoparticle where the Taurolidine is Contained within a Porous Silicate Sphere or a Carbon Nanotube Where the taurolidine is contained within a porous silicate sphere or a carbon nanotube, the porous silicate sphere or carbon nanotube preferably has a size of from 10 nm to 1000 nm. The porous silicate sphere or nanotube is thoroughly cleaned and sterilized prior to filling and coating. The taurolidine solution or suspension is prepared and the lipophilicity of the porous silicate sphere or nanotube facilitates filling the porous silicate sphere or nanotube with the taurolidine solution or suspension.

The filled spheres or nanotubes are then coated with a coating of a solid, slowly absorbing polymer, e.g., one comprising polylactide or polylactate. In one preferred form of the invention, the filled spheres or nanotubes are coated with a polysaccharide that will specifically bind to fungal mannoproteins. By way of example but not limitation, in one preferred form of the invention, the polysaccharide coating may comprise chitosan, starch or alginate. The sealing coating (e.g., polylactide, polylactate or polysaccharide) may be coated onto the filled spheres or nanotubes through a spray-drying process.

The nanoparticles are then mixed into a suitable pharmaceutical carrier, e.g., a fluid, for delivery to the blood. In one preferred form of the invention, the suitable pharmaceutical carrier may comprise a hyaluronic acid hydrogel.

3.4 Mechanism of Antifungal Action of the Taurolidine Nanoparticle

In use, the pharmaceutical composition (e.g., the carrier and the taurolidine-containing nanoparticles) are introduced into the bloodstream of the patient. As the pharmaceutical composition passes from the point of entry to the site of the *C. auris* infection, the hydrolysable polymer coating covering the taurolidine core acts as a sort of sacrificial layer, slowly breaking down over time as the nanoparticle makes its way through the bloodstream. Eventually the hydrolysable polymer coating breaks down to the point where the taurolidine core is exposed to the blood. The taurolidine core then hydrolyzes into its active moieties (the methylol derivatives) which target the *C. auris* infection.

In the case where the nanoparticles comprise an outer coating which comprises a polysaccharide which will specifically bind to fungal mannoproteins, once the taurolidine nanoparticle encounters the fungal cell wall, the outer polysaccharide coating of the nanoparticle binds to the mannoproteins of the fungus, and Brownian motion provides the energy for the fungal cell wall to unplug the pores in the nanoparticle. With the pores unplugged, the taurolidine oil solution or suspension is released and the taurolidine dissolves in the blood or tissue water. Once the taurolidine is exposed to water, it hydrolyzes into the active moieties (the methylol derivatives) which are created in the immediate vicinity of the fungal cell wall. This hyper-local delivery of the active moieties of the taurolidine enhances the selectivity of taurolidine for target microbes.

4. Parenteral Delivery System with Polymeric Carriers (e.g., PEG's)

In another form of the invention, the parenteral delivery system may comprise taurolidine, and/or taurolidine derivatives, which is/are bound to a polymer for delivery to the therapy site, e.g., where the taurolidine, and/or taurolidine derivatives, is/are bound to polyethylene glycol (PEG) for delivery to the therapy site.

In one preferred form of the invention, the taurolidine, and/or the taurolidine derivatives, is/are dispersed in a polymer-carbohydrate-lipid conjugate (or a combination of polymer-carbohydrate-lipid conjugates), such as a PEG-carbohydrate-lipid conjugate (or a combination of PEG-carbohydrate-lipid conjugates), to formulate drug compositions to increase the solubility of, or to increase the dispersivity of, and to enhance the stability of, and to delay the hydrolysis of, the taurolidine, and/or the taurolidine derivatives, so as to provide long lasting antimicrobial action.

In one form of the invention, a novel pharmaceutical composition for parenteral administration of taurolidine, and/or taurolidine derivatives, is provided, wherein the novel pharmaceutical composition comprises:
  a) an aqueous solution or mixture of a polymer-carbohydrate-lipid conjugate or a combination of polymer-carbohydrate-lipid conjugates (e.g., comprising a PEG-carbohydrate-lipid conjugate or a combination of PEG-carbohydrate-lipid conjugates);
  b) taurolidine, and/or taurolidine derivatives; and
  c) a solubility enhancer comprising a polymer-carbohydrate-lipid conjugate or a combination of polymer-carbohydrate-lipid conjugates (e.g., comprising a PEG-carbohydrate-lipid conjugate or a combination of PEG-carbohydrate-lipid conjugates).

In one form of the present invention, the process for making a novel pharmaceutical composition for parenteral administration of taurolidine comprises the steps of:
  adding an aqueous solution of a polymer-carbohydrate-lipid conjugate or a combination of polymer-carbohydrate-lipid conjugates (e.g., a PEG-carbohydrate-lipid conjugate or a combination of PEG-carbohydrate-lipid conjugates) to a vessel;
  adding taurolidine, and/or derivatives of taurolidine, in liquid or slurry form to the vessel;
  mixing until the taurolidine, and/or derivatives of taurolidine, is/are visually dispersed in the aqueous solution of the polymer-carbohydrate-lipid conjugate or the combination of polymer-carbohydrate-lipid conjugates (e.g., the PEG-carbohydrate-lipid conjugate or the combination of PEG-carbohydrate-lipid conjugates);
  adding pre-dissolved excipients (e.g., polymer-carbohydrate-lipid conjugates such as PEG-carbohydrate-lipid conjugates) to the vessel; and
  mixing until a homogenous solution is achieved.

The present invention comprises various aqueous and polymer-carbohydrate-lipid based (e.g., PEG-carbohydrate-lipid based) formulations of poorly water soluble taurolidine, and/or taurolidine derivatives, which includes compositions for parenteral preparations such as intravenous injection. One aspect of the present invention comprises a solution of taurolidine, and/or taurolidine derivatives, and PEG-carbohydrate-lipid conjugates, to enhance the solubility of, or to increase the dispersivity of, taurolidine, and/or taurolidine derivatives, in aqueous solutions.

A preferred embodiment of the present invention may comprise an aqueous-based, injectable pharmaceutical composition including, but not limited to, taurolidine, and/or taurolidine derivatives, and oieoyltri-ethylenetetramine-polyethyleneglycol lactobionate (OTL-PEG) or oleoyldiethylenetetramine-dodecaethylene glycol lactobionate (ODL-PEG). In at least one aspect of the present invention, the solution includes taurolidine in concentrations ranging from 0.05 mg/mL to 50 mg/mL, and the ratio of PEG-carbohydrate-lipid to taurolidine ranges from 0.2 to 25 (w/v). In one form of the present invention, the concentration of taurolidine ranges from 0.5 mg/mL to 50 mg/mL. In one form of the present invention, the concentration of taurolidine ranges from 0.5 mg/mL to 10 mg/mL and the percent of PEG-carbohydrate-lipid conjugates ranges from 0.5 to 10 (w/v) of the total solution.

Further aspects of the present invention may provide aqueous, injectable taurolidine solutions in which the diluent consists of 0.5 to 25 percent (w/v) of the PEG-carbohydrate-lipid conjugates and 75 to 99.5 percent (v/v) of water or a buffer or saline or dextrose solution. Also preferable are aqueous, injectable taurolidine solutions in which 85 to 99 percent (v/v) of the total solution is water or a buffer or saline or dextrose solution.

In one form of the present invention, the aqueous injectable taurolidine solutions comprise taurolidine in a lipid cubic phase (LCP) including, but not limited to, OTL-PEG or ODL-PEG plus aqueous media, at concentrations of taurolidine ranging from 0.5 mg/mL to 50 mg/mL, 0.5 to 25 percent (w/v) of PEG-carbohydrate-lipid conjugates, and 75 to 99.5 percent (v/v) water, wherein the concentration of taurolidine in the combined solution ranges from 0.5% to 5%.

The aqueous injectable taurolidine solutions of the present invention may be administrated by bolus injection or by infusion. Infusion may be preferable for such solutions where the concentration of taurolidine is greater than 0.01 mg/mL. In the case of infusion, the length of an infusion may be, preferably, 30 minutes to 6 hours and may, preferably, not be more than 24 hours.

Aspects of the present invention may involve solubilizing the taurolidine by using one or more amphipathic PEG conjugates. A combination of (i) taurolidine (and/or taurolidine derivatives) in LCP, plus the PEG-carbohydrate-lipids, and (ii) polysorbates, may be preferred solubilizing agents, in which acyl chains comprise the lipophilic portion of the amphipathic PEG conjugate.

A branched PEG-carbohydrate-lipid conjugate may also be an excellent solubilizing agent, in which the PEG polymer comprises more than single PEG chains of the conjugate. Similarly, branched PEG-carbohydrate-lipid conjugates may also be used as solubilizing agents. As with LCP solubilizing agents, these compounds typically are waxy solids or semisolids at the temperature of solubilization, and these PEG-carbohydrate-lipid conjugates typically have melting points above about 25 degrees C. Such solubilizing agents may also be used to prepare IV formulations and oral or topical liquids. A first step for solubilization may comprise combining the taurolidine with (an) amphipathic PEG conjugate(s) which may be semisolid or solid at the temperature of solubilization. For formulating the taurolidine solution at room temperature (which may be preferred), a concentrated solution of a PEG-carbohydrate-lipid conjugate may be desired. Such solubilization may be done by first adding the liquid form of the taurolidine to the concentrated solution of the PEG-carbohydrate-lipid conjugates. The aqueous solution may be further diluted with water or a buffer. Alternatively, the taurolidine may be pre-dissolved in a small amount of acid, base or alcohol, then mixed with the PEG-carbohydrate-lipid conjugates in aqueous solution.

By performing solubilization at elevated temperatures, PEG-carbohydrate-lipid conjugates with higher melting temperatures may be used as solubilizing agents. When forming aqueous solutions, the aqueous solution may also be preferably added at an elevated temperature.

If a terminal group is attached to the PEG chain, it may comprise a wide variety of chemical moieties. Such moieties may have a molecular weight of less than 650. Such moieties include $-NH_2$, $-COOH$, $-OCH_2CH_3$, $-OCH_2CH_2OH$, $-COCH=CH_2$, $-OCH_2CH_2NH_2$, $-OSO_2CH_3$, $-OCH_2C_6H_6$, $-OCH_2COCH_2CH_2COONC_4H_4O_2$, $-CH_2CH_2=CH_2$, $-C_{10}Hi_6N_2O_3S$ and $-OC_6H_6$. The terminal group may be a functional group that facilitates linking taurolidine to the surface of lipid vesicle aggregates. Amino acids, amino alkyl esters, biotins, maleimide, diglycidyl ether, maleinimido propionate, methylcarbamate, tosylhydrazone salts, azide, propargyl-amine, propargyl alcohol, NHS esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt may be useful for such linking.

Linked therapeutic and targeting agents may include Fab fragments (fragment antigen-binding), cell surface binding agents, and the like. Additionally, the terminal group may include functional cell-targeting ligands such as folate, transferrin and molecules such as monoclonal antibodies, ligands for cellular receptors or specific peptide sequences may be attached to the liposomal surface to provide specific binding sites. The terminal group may be neutral or include either negatively or positively charged head-groups such as decanolamine, octadecylolamine, octanolamine, butanolamine, dodecanolamine, hexanolamine, tetradecanolamine, hexadecanolamine, oleylamine, decanoltrimethylaminium, octadecyloltrimethylaminium, octanoltrimethylaminium, butanoltrimethylaminium, dodecanoltrimethylaminium, hexanoltrimethylaminium, tetradecanoltrimethylaminium, hexadecanoltrimethylaminium, and/or oleyltrimethylaminium, for example. Other useful R groups include alkyl groups such as alkoxy moieties, amino acids, and sugars including monosaccharides, disaccharides, tri-saccharides and the oligosaccharides-containing 1, 2, 3, and 4 or more monosaccharide units respectively. Additionally, targeting moieties such as antibody fragments and vitamins may also be used as R groups. Generally, the R group may be highly soluble in water. The molecular weight of the R group may be less than about 650 Daltons (Da), and for most applications the R group may be easily polarized, to increase the binding and interaction with proteins at the targeted sites.

Mixtures of PEG-carbohydrate-lipid conjugates may be used in the present invention where combinations of PEG-carbohydrate-lipid conjugates are used, and the properties of the lipid mixture (e.g., melting point or average size of the PEG chain) may be calculated by known methods or determined empirically.

The manufacture of the parenteral solution may comprise first adding taurolidine to a concentrated PEG-carbohydrate-lipid conjugate solution and mixing until homogenous, which may be accomplished at room temperatures. Next, pre-mixed aqueous preparations may be added to the lipid-taurolidine mixture and mixed until a homogenous solution is obtained. The solution may then be filtered for sterility while maintaining an overlay of sterile-filtered nitrogen during the process. Appropriate volumes of the solution may be filled into ampules and sealed using aseptic technique. Sterile conditions may be maintained throughout the filtering, filling, and sealing operations in accordance with standard manufacturing procedures for injectables. While the formulated product may be stable at room temperature, it may be preferably stored under refrigeration for extended shelf life.

A preservative may be desired when the sterile-filtered process is prevented by high concentrations of the PEG-carbohydrate-lipid conjugates, the possible preservatives may be selected from a group of antimicrobial agents consisting of benzyl alcohol, chlorobutanol, methylparaben, propylparaben, phenol, ethylenediaminetetraacetic acid, and m-cresol.

In one aspect of the present invention, a novel pharmaceutical composition for administration by intravenous injection is provided. The novel pharmaceutical composition comprises an aqueous solution; a PEG-carbohydrate-lipid conjugate or a combination of PEG-carbohydrate-lipid conjugates; and taurolidine at a concentration of between about 0.05 mg/mL and about 50 mg/mL. The ratio of the PEG-carbohydrate-lipid conjugates to the taurolidine may be between about 0.2 and 25 (w/v). The average molecular weight of the PEG chains in the PEG-carbohydrate-lipid conjugate (or a mixture of PEG-carbohydrate-lipid conjugates) may be less than about 1500 Daltons (Da). The concentration of the taurolidine may preferably be between about 0.2 mg/ml to 50 mg/ml. The concentration of the PEG-carbohydrate-lipid conjugate may preferably be between about 0.5 to 25 percent (w/v) of the total solution.

In another aspect of the present invention, the invention provides a method of making a pharmaceutical composition suitable for administration by intravenous injection. The method comprises mixing a PEG-carbohydrate-lipid conjugate, or a combination of PEG-carbohydrate-lipid conjugates, with taurolidine and adding an aqueous solution while mixing to create a suspension. The final concentration of the taurolidine may preferably be between about 0.05 mg/ml and about 50 mg/ml. The ratio of the total PEG-carbohydrate-lipid conjugates to the taurolidine may preferably be between about 0.2 and 25 (w/v). The average molecular weight (MW) of the PEG chains in the PEG-carbohydrate-lipid conjugate, or combination of PEG-carbohydrate-lipid conjugates, may preferably be less than about 1500 Daltons (Da). The method may further comprise sealing the aqueous suspension in a sterile container or adding antimicrobial preservatives.

In another aspect of the present invention, there is provided a novel method for treating a disease in a mammal is provided. The novel method comprises preparing a novel pharmaceutical composition comprising an aqueous solution, a PEG-carbohydrate-lipid conjugate, or a combination of PEG-carbohydrate-lipid conjugates, and taurolidine at a concentration between about 0.05 mg/mL and about 50 mg/mL. The ratio of the PEG-carbohydrate-lipid conjugates to the taurolidine may be between about 0.2 and 25 (w/v). The novel pharmaceutical composition may be administered to the mammal intravenously. The average molecular weight (MW) of single PEG chains in the PEG-carbohydrate-lipid conjugate, or combination of PEG-carbohydrate-lipid conjugates, is preferably less than about 1500 Daltons (Da). The concentration of taurolidine may be between about 0.2 mg/mL to 25 mg/mL. The concentration of the PEG-carbohydrate-lipid conjugates may be between about 0.5 to 25 percent (w/v) of the total solution. The novel pharmaceutical composition may further comprise preservatives, where the concentration of preservatives may be between about 0.1 to 2% (w/v).

4.1 the PEGylation of Taurolidine

PEGylation is the process of attaching the strands of the polymer PEG to taurolidine. It produces alterations in the physiochemical properties including changes in conformation, electrostatic binding, hydrophobicity, etc. These physical and chemical changes increase systemic retention of the taurolidine. Also, it can influence the binding affinity of the therapeutic moiety of the taurolidine to the cell receptors and can alter the absorption and distribution patterns.

PEGylation, by increasing the molecular weight of the taurolidine, can impart several significant pharmacological advantages over the unmodified form, such as:
  improved taurolidine solubility;
  reduced dosage frequency, without diminished efficacy with potentially reduced toxicity;
  extended circulating life;
  increased taurolidine stability; and
  enhanced protection from proteolytic degradation.

PEG is a particularly attractive polymer for conjugation with taurolidine. The specific characteristics of PEG moieties relevant to taurolidine applications are:
  water solubility;
  high mobility in solution;
  lack of toxicity and low immunogenicity;
  ready clearance from the body; and
  altered distribution in the body.

4.2 the PEGylation Process of Taurolidine

The first step of the PEGylation of taurolidine is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional". The chemically active or activated derivatives of the PEG polymer are prepared to attach the PEG to taurolidine.

In general, PEGylation processes can be broadly classified into two types, namely a solution phase batch process and an on-column fed-batch process. The simple and commonly adopted batch process involves the mixing of reagents together in a suitable buffer solution, preferably at a temperature of between 4 degrees C. and 6 degrees C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems.

The choice of the suitable functional group for the PEG derivative is based on the type of available reactive group on the molecule that will be coupled to the PEG.

The techniques used to form first generation PEG derivatives are generally reacting the PEG polymer with a group that is reactive with hydroxyl groups, typically anhydrides, acid chlorides, chloroformates and carbonates. In second generation PEGylation chemistry, more efficient functional groups such as aldehyde, esters, amides, etc. are made available for conjugation.

As applications of PEGylation have become more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

Third generation PEGylation agents, where the shape of the polymer has been branched, Y shaped or comb shaped, are available which show reduced viscosity and lack of organ accumulation.

Taurolidine may be PEGylated according to any of the aforementioned techniques.

5. Suspension of Solid Taurolidine-Containing, and/or Taurolidine Derivative-Containing, Particles In another form of the invention, a suspension of taurolidine-containing particles, and/or taurolidine derivative-containing particles, may be intravenously injected into the patient to treat candidiasis in the bloodstream. In this form of the invention, the suspension may be formed by mixing taurolidine-containing particles, and/or taurolidine derivative-containing particles, into a hyaluronic acid hydrogel.

6. Pro-Drug Providing Taurolidine and/or Taurolidine Derivatives

In another form of the invention, a pro-drug providing taurolidine and/or a taurolidine derivative, may be intravenously injected into the patient to treat candidiasis in the bloodstream. In this form of the invention, the pro-drug may comprise a molecule to which the taurolidine, and/or a taurolidine derivative, is chemically bonded and which, when "cleaved off", will release the taurolidine or taurolidine derivative.

7. Taurolidine-Containing, and/or Taurolidine Derivative-Containing, Solution Capable of Prolonging the Effect of Taurolidine In another form of the invention, a taurolidine-containing, and/or taurolidine derivative-containing, solution capable of prolonging the effect of taurolidine, may be intravenously injected into the patient so as to treat candidiasis in the bloodstream. In this form of the invention, the solution may comprise taurolidine, and/or taurolidine derivatives, and a hyaluronic acid hydrogel.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for treating *Candida* auris in blood of a patient, the method comprising:
  providing taurolidine in powder form;
  forming a suspension of the powder form of taurolidine wherein the concentration of taurolidine in the suspension is one from the group consisting of about 0.5%, 1.0%, 2.0% and 4.0% w/v; and
  parenterally delivering the suspension to the blood of the patient to treat *C. auris* in the blood of the patient.

2. A method according to claim 1 wherein the suspension is buffered to the pH of blood.

3. A method according to claim 1 wherein the suspension further comprises substances that increase cellular permeability of the suspension.

4. A method according to claim 1 wherein the suspension further comprises anticoagulants.

5. A method according to claim 1 wherein the powder form of taurolidine is suspended in water.

6. A method according to claim 1 wherein the powder form of taurolidine is suspended in saline.

7. A method according to claim 1 wherein the suspension is delivered intravenously.

8. A method for treating *Candida auris* in blood of a patient, the method comprising:
providing taurolidine in powder form;
forming a solution of the powder form of taurolidine wherein the concentration of taurolidine in the solution is one from the group consisting of about 0.5%, 1.0%, 2.0% and 4.0% w/v; and
parenterally delivering the solution to the blood of the patient to treat *C. auris* in the blood of the patient.

9. A method according to claim 8 wherein the solution is buffered to the pH of blood.

10. A method according to claim 8 wherein the solution further comprises substances that increase cellular permeability of the solution.

11. A method according to claim 8 wherein the solution further comprises anticoagulants.

12. A method according to claim 8 wherein the powder form of taurolidine is suspended in water.

13. A method according to claim 8 wherein the powder form of taurolidine is suspended in saline.

14. A method according to claim 8 wherein the solution is delivered intravenously.

* * * * *